(12) United States Patent
Mande et al.

(10) Patent No.: US 12,142,349 B2
(45) Date of Patent: *Nov. 12, 2024

(54) METHOD AND SYSTEM FOR IDENTIFICATION OF KEY DRIVER ORGANISMS FROM MICROBIOME / METAGENOMICS STUDIES

(71) Applicant: Tata Consultancy Services Limited, Mumbai (IN)

(72) Inventors: Sharmila Shekhar Mande, Pune (IN); Kuntal Kumar Bhusan, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 1382 days.

This patent is subject to a terminal disclaimer.

(21) Appl. No.: 16/411,849

(22) Filed: May 14, 2019

(65) Prior Publication Data

US 2019/0348150 A1    Nov. 14, 2019

(30) Foreign Application Priority Data

May 14, 2018  (IN) .............................. 201823018040

(51) Int. Cl.
  *G16B 20/40*    (2019.01)
  *G16B 30/10*    (2019.01)
  *G16B 45/00*    (2019.01)

(52) U.S. Cl.
  CPC .............. *G16B 20/40* (2019.02); *G16B 30/10* (2019.02); *G16B 45/00* (2019.02)

(58) Field of Classification Search
  None
  See application file for complete search history.

(56) References Cited

U.S. PATENT DOCUMENTS

| 2012/0185227 | A1  | 7/2012 | Nikolskaya et al. |
| 2014/0207385 | A1* | 7/2014 | Martin ................... G16B 99/00 702/19 |
| 2015/0211078 | A1* | 7/2015 | Apte .................... C12Q 1/6888 506/2 |

FOREIGN PATENT DOCUMENTS

| CA | 2911416 | 11/2014 |
| WO | WO-2011/022660 | 2/2011 |
| WO | WO-2014/005094 | 1/2014 |

OTHER PUBLICATIONS

Faust, K. et al. (Aug. 2012). "Microbial interactions: from networks to models," *Nature Reviews Microbiology*, vol. 10; pp. 538-550.
Faust, K. et al. (Jul. 2012). "Microbial Co-occurrence Relationships in the Human Microbiome," *PLoS Computational Biology*, vol. 8, No. 7; pp. 1-17.
Package 'ccrepe', 9 pages (2024).

* cited by examiner

*Primary Examiner* — Joseph Woitach
(74) *Attorney, Agent, or Firm* — Finnegan, Henderson, Farabow, Garrett & Dunner, LLP

(57) ABSTRACT

The present disclosure addresses the technical problem related to the identification of microbial basis of a disease in microbiome. A system and method for identification of key driver responsible for bringing a change in a microbial population has been disclosed. A subset of common taxa between the 'control' and 'case' dataset is chosen and corresponding microbial association network is created. The method involves the characterization of the important community level changes between two association networks ('control' and 'case') that are obtained for a particular disease or condition. A taxon in the diseased state with an altered set of associations (identified by a high network shift score), while still being increasingly important (identified with a positive increase in betweenness) for the whole network, necessarily holds a key significance in the identification of key driver.

14 Claims, 15 Drawing Sheets

| Biological insight | Jaccard Index | NESH score |
|---|---|---|
| Node has similar count of neighbors with varying interacting partners (which may or may not be overlapping) | 1 | 0 |
| | 0 | 2.33 |
| | 0.43 | 1.19 |

FIG. 3A

| Biological insight | Jaccard Index | NESH score |
|---|---|---|
| Node has lower number of neighbors in case network with varying interacting partners (which may or may not be overlapping) | 0 | 1.83 |
| | 0.125 | 1.46 |
| | 0.5 | 0.5 |

FIG. 3C

Saliva HIV data      Plaque HIV data

METHOD AND SYSTEM FOR IDENTIFICATION OF KEY DRIVER ORGANISMS FROM MICROBIOME / METAGENOMICS STUDIES

PRIORITY CLAIM

This U.S. patent application claims priority under 35 U.S.C. § 119 to India Application No. 201823018040, filed on May 14, 2018. The entire contents of the aforementioned application are incorporated herein by reference.

TECHNICAL FIELD

The embodiments herein generally relates to the field of detection of key driver micro-organism, and, more particularly, to a method and system for the identification of key driver organisms responsible for bringing changes in a microbial population corresponding to a micro-biome associated disease.

BACKGROUND

In the recent times, major advances has been observed in the field of genomics and other high throughput biology. Various ecological studies have been performed to analyze the DNA samples to detect driver organisms responsible for a disease. Generally, the samples are collected from several different environments and abundances of different microbial species in the respective environments are analyzed. In some cases, these environments can represent micro-biota associated with human body such as lung, gut, skin etc. Here, different environments can exemplify different health conditions for example, healthy and diseased. In such cases, comparison between two microbial association networks holds key information to reveal 'driver' species which have a critical role in onset and progression of the disease.

Current methods intended to identify the microbial basis of a disease rely on construction of matrices of microbial abundances. For example, a study aiming to associate one or more microbe to a disease would identify the statistically differentially abundant ones in the diseased state with respect to the healthy. However, the combined effect of the mutual association and inhibition within the residing microbial communities plays an even bigger role in determining particular characteristics which cannot be quantified by these differential abundance analyses. Available methods for quantifying these changes in microbial association patterns rely on creating microbial association networks from the abundance data and subsequently compare their network properties. However, in most of the cases, these global graph property measures fail to scrutinize changes endured by individual nodes in the two representative networks In another method, one can compare two association networks by comparing local network properties like degree and betweenness. However, these local network properties mainly depend on the number of edges passing through a particular node. Such analyses however only provide a qualitative measure of the compared properties and completely ignore the constituent members. Similarly, global properties also cannot be used directly to compare two networks in a situation where the number of nodes and edges in the two networks are comparative but connections between nodes are entirely different, i.e., in case of network rewiring. In other words, two networks may look very similar while comparing their traditional network properties yet may be very different owing to the fact that individual nodes have an entirely different set of edges in the two environments. Special analysis methods are hence required to analyze such networks.

Methods used to calculate differentially abundant genera between two conditions (e.g., control and disease) rely only on the genera abundance information and completely ignore the inter-microbial interactions. However, the combined effect of the mutual association and inhibition within the residing microbial communities are known to play important roles in influencing the disease state and propagation, which gets completely ignored by such methodologies.

There is a need to characterize important community level changes between two association networks, such as control and case that are obtained for a particular disease or condition. Furthermore, in order to correctly assess the network rewiring, it is often helpful to work with sub-networks of common participant nodes rather than the whole networks.

SUMMARY

Embodiments of the present disclosure present technological improvements as solutions to one or more of the above-mentioned technical problems recognized by the inventors in conventional systems. For example, in one embodiment, a system has been provided for identification of key driver responsible for bringing a change in a microbial population. The system comprises an input module, an extractor, a sequencer, a memory and a processor. The input module receives a sample from a first set of individuals and a second set of individuals. The extractor extracts DNA samples from the sample from the first set and the second set of individuals. The sequencer sequences the DNA from the samples corresponding to the first set and the second set of individuals using a sequencer to generate a plurality of DNA sequences. The processor further comprises a DNA filtration module, a matrix creation module, a matrix filtration module, a network generation module, a network filtration module, a microbial community identification module, a Jaccard edge index calculation module, a community shuffling plot construction module, a betweenness computation module, a coreness calculation module, a quantification module, a neighbor shift (abbreviated by NESH) score calculation module, a network pair identification module and a key driver identification module. The DNA filtration module filters and processes the plurality of DNA sequences corresponding to the first set and the second set of individuals for removing low quality DNA sequences and non-essential DNA fragments. The matrix creation module creates two matrices of microbial abundance profile of the plurality of DNA sequences corresponding to the first set and the second set of individuals, wherein each matrix of microbial abundance profile includes abundances of microbial organisms corresponding to individuals belonging to corresponding to the first set and the second set of individuals. The matrix filtration module filters the matrices to retain microbes which are common to both the matrices corresponding to the first set and the second set of individuals. The network generation module generates a first network and a second network by representing microbial organisms in each matrix as a network of plurality of nodes corresponding to the first set and the second set of individuals. The network filtration module filters the first network and the second network to retain a set of nodes common to both the networks. The microbial community identification module identifies distinct microbial communities from the first network and the second network generated from the first and the second set of individuals. The Jaccard edge index calculation module calculates a Jaccard edge index between the first and the second network. The community shuffling plot construction module constructs a community shuffling plot using the identified distinct microbial communities. The betweenness computation module computes a scaled change in betweenness from the first network to the second for each of the nodes common to the first network and the second network. The coreness calculation module calculates a value of coreness for each of the nodes corresponding to the first network and the second network, wherein the value of coreness indicates the importance of the node in the network. The quantification module quantifies the community shuffling and network rewiring based on the community shuffling plot and the calculated Jaccard edge index respectively. The NESH score calculation module calculates a neighbor shift score for each of the nodes common to the first network and the second network using a predefined formula. The network pair identification module identifies whether the filtered network pair: have undergone community shuffling based on a predefined split in the communities between the first network and the second network using the community shuffling plot and individual community members (nodes) based on change in the value of coreness, and have undergone rewiring based on the value of Jaccard edge index. The key driver identification module identifies a node as a key driver from the first network to the second network based on a predefined condition on the values of the neighbor shift score and the scaled change in betweenness.

In another aspect the embodiment here provides a method for identification of key driver responsible for bringing a change in a microbial population. Initially, a sample from a first set of individuals and a second set of individuals is obtained. In the next step, DNA samples are extracted from the sample from the first set and the second set of individuals. The extracted DNA samples corresponding to the first set and the second set of individuals is then sequenced using a sequencer to generate a plurality of DNA sequences (206). In the next step, the plurality of DNA sequences corresponding to the first set and the second set of individuals is filtered and processed for removing low quality DNA sequences and non-essential DNA fragments. In the next step, two matrices of microbial abundance profile of the plurality of DNA sequences corresponding to the first set and the second set of individuals are created, wherein each matrix of microbial abundance profile includes abundances of microbial organisms corresponding to individuals belonging to corresponding to the first set and the second set of individuals. In the next step, the matrices are filtered to retain microbes which are common to both the matrices corresponding to the first set and the second set of individuals. In the next step, a first network and a second network is generated by representing microbial organisms in each matrix as a network of plurality of nodes corresponding to the first set and the second set of individuals. The generated first network and the second network are then filtered to retain a set of nodes common to both the networks. In the next step, distinct microbial communities are identified from the first network and the second network generated from the first and the second set of individuals. In the next step, a Jaccard edge index is calculated between the first network and the second network. In the next step a community shuffling plot is constructed using the identified distinct microbial communities. In the next step, a scaled change in betweenness from the first network to the second network is computed for each of the nodes common to the first network and the second network. Further, a value of coreness is calculated for each of the nodes corresponding to the first network and the second network, wherein the value of coreness indicates the importance of the node in the network. In the next step, the community shuffling and network rewiring are quantified based on the community shuffling plot and the calculated Jaccard edge index respectively. In the next step, a neighbor shift score is calculated for each of the nodes common to the first network and the second network using a predefined formula. In the next step, it is identified whether the filtered network pair have undergone community shuffling based on a predefined split in the communities between the first network and the second network using the community shuffling plot and individual community members (nodes) based on change in the value of coreness, and have undergone rewiring based on the value of Jaccard edge index. And finally, a node is identified as a key driver from the first network to the second network based on a predefined condition on the values of the neighbor shift score and the scaled change in betweenness.

In another aspect the embodiment here provides one or more non-transitory machine readable information storage mediums comprising one or more instructions which when executed by one or more hardware processors cause identification of key driver responsible for bringing a change in a microbial population. Initially, a sample from a first set of individuals and a second set of individuals is obtained. In the next step, DNA samples are extracted from the sample from the first set and the second set of individuals. The extracted DNA samples corresponding to the first set and the second set of individuals is then sequenced using a sequencer to generate a plurality of DNA sequences (206). In the next step, the plurality of DNA sequences corresponding to the first set and the second set of individuals is filtered and processed for removing low quality DNA sequences and non-essential DNA fragments. In the next step, two matrices of microbial abundance profile of the plurality of DNA sequences corresponding to the first set and the second set of individuals are created, wherein each matrix of microbial abundance profile includes abundances of microbial organisms corresponding to individuals belonging to corresponding to the first set and the second set of individuals. In the next step, the matrices are filtered to retain microbes which are common to both the matrices corresponding to the first set and the second set of individuals. In the next step, a first network and a second network is generated by representing microbial organisms in each matrix as a network of plurality of nodes corresponding to the first set and the second set of individuals. The generated first network and the second network are then filtered to retain a set of nodes common to both the networks. In the next step, distinct microbial communities are identified from the first network and the second network generated from the first and the second set of individuals. In the next step, a Jaccard edge index is calculated between the first network and the second network. In the next step a community shuffling plot is constructed using the identified distinct microbial communities. In the next step, a scaled change in betweenness from the first network to the second network is computed for each of the nodes common to the first network and the second network. Further, a value of coreness is calculated for each of the nodes corresponding to the first network and the second network, wherein the value of coreness indicates the importance of the node in the network. In the next step, the community shuffling and network rewiring are quantified based on the community shuffling plot and the calculated Jaccard edge index respectively. In the next step, a neighbor shift score is calculated for each of the nodes common to the first network and the second network using a predefined formula. In the next step, it is identified whether the filtered network pair have undergone community shuffling based on a predefined split in the communities between the first network and the second network using the community shuffling plot and individual community members (nodes) based on change in the value of coreness, and have undergone rewiring based on the value of Jaccard edge index. And finally, a node is identified as a key driver from the first network to the second network based on a predefined condition on the values of the neighbor shift score and the scaled change in betweenness.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 3A, 3B and 3C represents three categories correspond to conditions where a node has a similar, higher and lower number of interacting partners between the compared networks respectively according to an embodiment of the disclosure.

DETAILED DESCRIPTION

Figure 1:
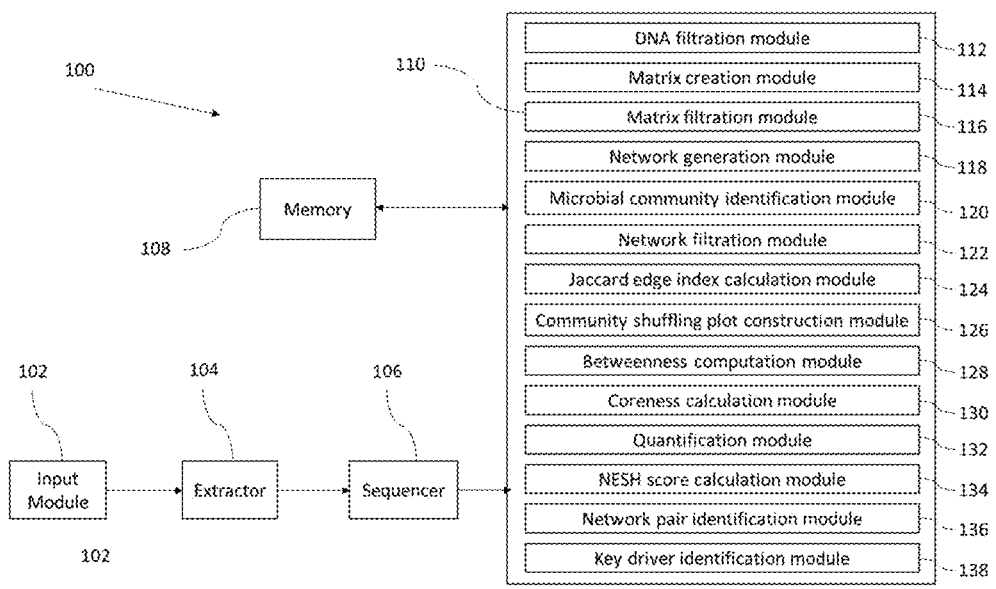
FIG. 1 illustrates a block diagram of a system for identification of key driver responsible for bringing a change in a microbial population according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 11, where similar reference characters denote corresponding features consistently throughout the figures, there are shown preferred embodiments and these embodiments are described in the context of the following exemplary system and/or method.

According to an embodiment of the disclosure, a system 100 for the identification of key driver responsible for bringing changes in a microbial population is shown in the block diagram of FIG. 1. The key driver is an organism or species which have a critical role in onset and progression of the disease. The system 100 is configured to compare a case-control study for the healthy and the diseased set of individuals. The disclosure provides an updated workflow (hereafter referred to as 'NetShift') to identify key driver responsible for bringing changes in the microbial population.

In the present disclosure, the subset of common taxa between the 'control' and 'case' dataset are chosen and the corresponding microbial association network was created using a modified method. This method which does not require a prior Cumulative Sum Scaling (CSS) normalization of the data. As Cumulative Sum Scaling (CSS) normalization in some cases might cause artifacts. Further, the present disclosure, does not make use of a plot of Jaccard node vs. Jaccard edge to decipher network rewiring, instead a new way of community shuffling analysis has been disclosed. Further, the earlier assumption of maximum degree of a node in a network was set to 10 while calculating the neighbor shift score, which in this current communication is calculated directly from the network. This makes the modified network shift score a general case applicable to any microbiome case-control network pair and the score disclosed in the earlier filing a special case of the current modified score.

The objective of the updated NetShift workflow is to characterize important community level changes between two association networks ('control' and 'case') that are obtained for a particular disease or condition and subsequently identify key microbial taxa. The methodology considers following three points (1) Overall change in the interaction or community pattern between the control and case (disease) states (2) Any major changes in association of a node (taxon) between the two states. And (3), if there is any major change, then it is identified that the node (taxon) has been an important member of the community or not and whether there is an increase in its importance in the case (disease) state.

According to an embodiment of the disclosure, the system 100 further comprises an input module 102, a DNA extractor 104, a sequencer 106, a memory 108 and a processor 110 as shown in the block diagram of FIG. 1. The processor 110 works in communication with the memory 108. The processor 110 further comprises a plurality of modules. The plurality of modules accesses the set of algorithms stored in the memory 108 to perform a specific task. The processor 110 further comprises a DNA filtration module 112, a matrix creation module 114, a matrix filtration module 116, a network generation module 118, a microbial community identification module 120, a network filtration module 122, a Jaccard edge index calculation module 124, a community shuffling plot calculation module 126, a betweenness computation module 128, a coreness calculation module 130, a quantification module 132, a NESH score calculation module 134, a network pair identification module 136 and a key driver identification module 138.

According to an embodiment of the disclosure, the system 100 is primarily configured to receive human micro-biome samples from two different classes of human subjects, namely case and control. In another embodiment, the system 100 can also collect the micro-biome samples from any two different environments not restricted to human micro-biome only. Further in yet another embodiment, the system 100 can collect the micro-biome samples from a single environment at two or more different time-points.

According to an embodiment of the disclosure the input module 102 is configured to provide an input to the system 100. The input module 102 is configured to receive the sample from a first set of the individuals and a second set of individuals. The sample is generally collected from different part of human body from different environments such as lung, gut, skin etc. It should be appreciated that the first set may be from diseased (case) 'D' individuals and the second set is from the healthy (control) 'H' individuals. In another embodiment, the first set of individuals is in a reference state and the second set of individuals are in a perturbed state. The input module 102 may include a variety of software and hardware interfaces. In an example, the input module 102 can be referred as the user interface or input/output interface 102. The I/O interface user may allow the system 100 to interact with the user directly or through the client devices. The input module 102 can facilitate multiple communications within a wide variety of networks and protocol types, including wired networks, for example, LAN, cable, etc., and wireless networks, such as WLAN, cellular, or satellite. The input module 102 may include one or more ports for connecting a number of devices including assistive technology devices or adaptive products used by people with disability to one another or to another server.

The samples received from the first and the second set of individuals is utilized to extract DNA samples from them using the DNA extractor 104. Further, the DNA samples are then sequenced using the sequencer 106. The sequencing is performed using high-throughput sequencing techniques. The sequencing results in the generation of a plurality of DNA sequences. In an embodiment, the sequencer 106 subsequently, amplifies and sequences either full-length or specific variable regions of the bacterial 16S rRNA marker genes from the extracted microbial DNA. In another embodiment, the DNA samples can be amplified and sequenced to one or more phylogenetic marker genes other than (or in addition to) the 16S rRNA marker genes. A Whole Genome Shotgun (WGS) sequencing of the collected micro-biome is performed. In yet another embodiment, the sequencing is performed using approaches which involve either a fragment library, a mate-pair library, a paired-end library or a combination of the same.

The system 100 further includes the DNA filtration module 112. The DNA filtration module 112 is configured to filter the plurality of DNA sequences. The low quality sequences are removed using the DNA filtration module 112. The DNA filtration module 112 also clusters the similar sequences together. The DNA filtration module 112 also configured to remove the non-essential DNA fragments.

According to an embodiment of the disclosure the system 100 further comprises the matrix creation module 114. The matrix creation module 114 is configured to create two matrices of 'microbial abundance profile' of the plurality of DNA sequences corresponding to the samples derived from the first set of individuals and the second set of individuals. Each matrix of microbial abundance profile includes abundances of microbial organisms corresponding to individuals belonging to each set. The microbial abundance profile comprises of the abundance values of various individual 'taxonomic groups' present in the sequenced micro-biome sample. The rows of the matrices represent various taxonomic groups (hereafter referred to as 'taxon/taxa/genera') and the columns represent the presence of taxon in the corresponding samples. The creation of matrices corresponds to identification of counts of all potential microbes across the first set and second set of individuals using a marker gene survey data or whole genome sequence data.

According to another embodiment of the disclosure, the microbial abundance profile can be generated using assignment based taxonomic classification (binning) approaches which involve comparing sequence and/or compositional level similarity of obtained micro-biome sequence data against existing reference sequence databases. In yet another embodiment, initially the sequenced DNA data corresponding to 16S rRNA marker genes (or other phylogenetic marker genes) is computationally analyzed and then the microbial abundance profile can be generated by segregating the DNA sequences into Operational Taxonomic Units (OTUs). This segregation may be based on clustering sequences based on their level of sequence level similarity. In yet another embodiment the sequenced DNA data corresponding to either phylogenetic marker genes or WGS sequence data are computationally analyzed and the microbial abundance profile is generated by segregating/clustering the DNA sequences based on compositional similarity.

According to an embodiment of the disclosure, the system 100 also comprises the matrix filtration module 116. The matrix filtration module 116 is configured to filter the matrices to retain microbes which are common to both the matrices corresponding to the first set and the second set of individuals. The filtration of matrices corresponds to excluding any microbial data which is not present in both set of individuals or present below a minimum specified threshold. In an example, the minimum specified threshold is set to microbes present in at least 70% of the samples in each set.

In order to understand the salient features of any biological interaction network, it is important to first evaluate the inherent graph properties like clustering coefficient, density, average path length, etc. The average path length is the measure of the efficiency of information transport in a network, clustering coefficient indicates the tendency of a graph to be divided into clusters and is an important measure to study the community structure. Once the association networks corresponding to the 'control' and 'case' states for a particular physiological condition are available, a comparison of graph properties can be done if the two networks are sufficiently comparable.

According to an embodiment of the disclosure, the system 100 comprises the network generation module 118 and network filtration module 122. The network generation module 118 is configured to generate a first network and a second network by representing microbial organisms in each matrix as a network of plurality of nodes corresponding to the first set and the second set of individuals. The network filtration module 122 is configured to filter the first network and the second network to retain a set of nodes common to both the networks.

In an embodiment the microbial association network is generated using the network generation module 118 as follows: Initially, for matrix for the healthy state of individuals (MH), the array of each constituent taxa (T1 ... Tn) is extracted. After that, Pearson correlation, Spearman correlation, Bray-Curtis dissimilarity and Kullback-Leibler dissimilarity are calculated for taxon arrays of any particular pair of taxa. Followed by randomizing the taxa arrays and again calculating the aforementioned correlation/dissimilarity indices to generate a distribution of all four of these measures. In the next step, based on the distribution obtained in the previous step, the p-value of the original index is calculated. Only those edges are retained, which have an associated p-value less than 0.05. Then the edge between any two taxa is considered to be significant only if three out of four indices agree upon it. And finally, all edges quantified in the previous step are listed to get the microbial association network NH. The similar steps are repeated for matrix for the diseased state of individuals (MD) for diseased set of individuals and the microbial association network ND is obtained. In another implementation, the network can also be calculated using compositionality corrected by renormalization and permutation (CCREPE) method as taught by ES and Weingart G (2014). ccrepe: ccrepe_and_nc.score. R package version 1.15.0. Though use of any other method is well within the scope of this disclosure.

According to an embodiment of the disclosure, the system 100 further comprises the microbial community identification module 120. The microbial community identification module 120 is configured to identify distinct microbial communities from the first network and the second network generated from the first and the second set of individuals. The distinct microbial communities are identified using at least one of a fast greedy algorithm, an edge betweenness algorithm or a walk-trap algorithm. Though use of any other method is well within the scope of this disclosure.

According to an embodiment of the disclosure, the system 100 further comprises the Jaccard edge index calculation module 124. The Jaccard edge index calculation module 124 is configured to calculate a Jaccard edge index between the first and the second network. In an embodiment, the following formula can be used for the calculation:

$$\text{Jaccard edge index} = \frac{A_E \cap B_E}{A_E \cup B_E}$$

Where, $A_E$ and $B_E$ are the total edges in network A and B respectively. A represents to the first set of individuals and B represents to the second set of individuals.

According to an embodiment of the disclosure, the system 100 further comprises the community shuffling plot construction module 126. The community shuffling plot construction module 126 constructs a community shuffling plot using the identified distinct microbial communities.

The community shuffling plot highlights the changes in the communities between the two compared association networks. To generate the plot, a community detection algorithm is first used to separately assign a community membership to each node of the 'case' and 'control' networks. Subsequently, each community in the 'control' network is compared with every other community in the 'case' network and their similarities in terms of shared nodes are calculated. Finally, the all versus all similarity matrix between the case and control association network is represented as graphical chats.

Figure 4:
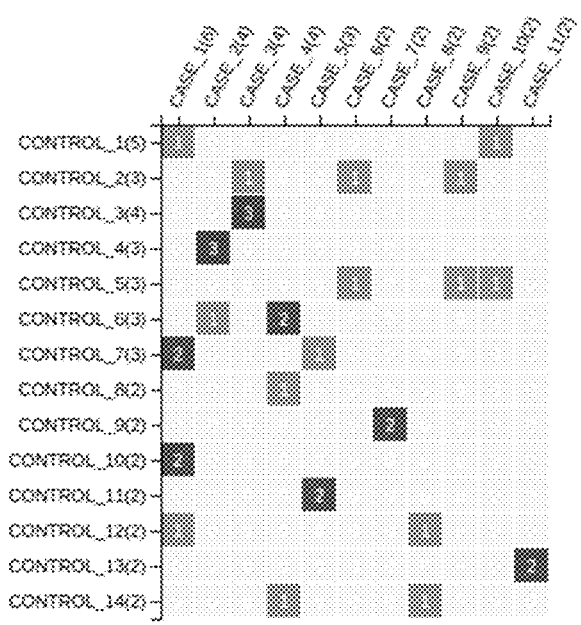
FIG. 4 shows a community shuffling heat-map for the allergy dataset showing changes in the community structure between the 'control' and 'case' datasets according to an embodiment of the disclosure.
Figure 5:
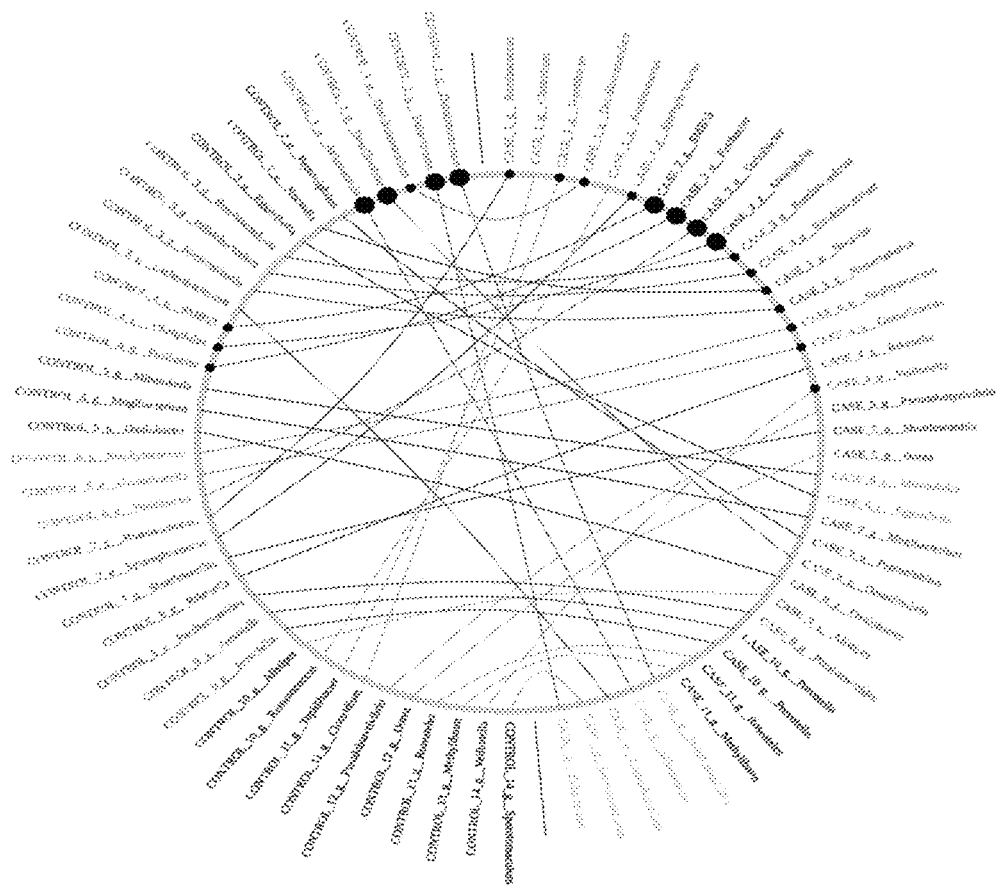
FIG. 5 shows a community shuffling graph for the allergy dataset showing two distinct 'core community hubs' in the control and case data where node sizes are mapped to 'coreness' values according to an embodiment of the disclosure.

The all versus all similarity between the control and case network is represented as a 'community shuffling plots' in form of heat-map and a network view. The heat-map displays the identified communities in the control and case network as rows (i) and columns (j) of a matrix with each cell representing the similarity ($S_{ij}$) between the $i^{th}$ control and $j^{th}$ case community. The value of $S_{ij}$ is obtained as the intersecting nodes between the node contents of the two communities is shown in FIG. 4 and FIG. 5. The size of each community in both the networks in terms of node size is displayed along with the label inside a parenthesis. The network view of community shuffling on the other hand allows visualizing the exact changes in the community members between the two networks. In the network view, the nodes belonging to the control network are plotted along the left half of a circle and the ones belonging to the case are plotted along the right half. The node labels in control are prefixed with 'CONTROL_community affiliation' and those of case are similarly prefixed with 'CASE_community affiliation'. Conserved communities display a lesser amount of criss-cross edges compared to the shuffled ones. Nodes in the network are mapped to their 'coreness' values by default allowing visualization of 'core communities' which can be changed to degree or betweenness using the available option.

More community splits (from 'Control' to 'Case') represents increased changes in microbial assembly rules. Hence, plots having less shuffling will show less horizontal splits (in the blocks) and individual blocks will have a higher cell value ($S_{ij}$).

According to an embodiment of the disclosure, the system 100 further comprises the betweenness computation module 128. The betweenness computation module 128 is configured to compute a scaled change in betweenness from the first network to the second network for each of the nodes common to the first network and the second network. Following formula is used for the scaled betweenness ($B_{scaled}$) for each of the nodes in both of the networks using the formula:

$$B_{scaled} = \frac{B_{calculated} - B_{min}}{B_{max} - B_{min}}$$

Where, $B_{calculated}$, $B_{min}$ and $B_{max}$ correspond to the calculated, min and max betweenness values. Further, scaled change in betweenness ($\Delta B^n$) is computed for each of the common nodes second set of individuals with respect to the microbial association network of the first set of individuals.

$$\Delta B^n = B_{scaled}{}^n{}_D - B_{scaled}{}^n{}_H$$

Where, $B_{scale}{}^n{}_D$ and $B_{scale}{}^n{}_H$ correspond to the scaled betweenness of node 'n' in diseased and healthy state respectively.

According to an embodiment of the disclosure, the system 100 further comprises the coreness calculation module 130. The coreness calculation module 130 is configured to calculate a value of coreness for each of the nodes corresponding to the first network and the second network, wherein the value of coreness indicates the importance of the node in the network. The distribution of the value of coreness in the first network and the second network are used to identify the communities having the highest change.

According to an embodiment of the disclosure, the system 100 further comprises the quantification module 132. The quantification module 132 is configured to quantify the community shuffling and network rewiring based on the community shuffling plot and the calculated Jaccard edge index respectively. The community shuffling is quantified using the community shuffling plot by viewing the splits of the communities from the first network to the second network.

According to an embodiment of the disclosure, the system 100 further comprises the NESH score calculation module 134. The NESH score calculation module 134 is configured to calculate the neighbor shift score for each of the nodes common to the first network and the second network using a predefined formula. In the present application, the calculation of NESH score has been modified to improve the overall accuracy of the system 100. The formula for calculating NESH score have been modified to accommodate the varying types of network comparisons. The NESH score for a node common to the control and case networks is calculated using the modified formula given below:

$$NESH_{A \to B} = 1 - \left\{ \left( \frac{[\text{Neighbors}]^A \cap [\text{Neighbors}]^B}{[\text{Neighbors}]^A \cup [\text{Neighbors}]^B} \right) - \left( \frac{[\text{Neighbors}]^B - [\text{Neighbors}]^A}{\text{Max degree in } B} + \frac{[\text{Neighbors}]^B - [\text{Neighbors}]^A}{[\text{Neighbors}]^B \cup [\text{Neighbors}]^A} \right) \right\}$$

Where A and B corresponds to the healthy (control) and disease (case) networks respectively. $[\text{Neighbors}]^A$ and $[\text{Neighbors}]^B$ represent the set of first neighbors of the considered node corresponding to A and B respectively. The score can be broken down into three components namely X, Y and Z.

$$\text{Where, } X = \frac{[\text{Neighbors}]^A \cap [\text{Neighbors}]^B}{[\text{Neighbors}]^A \cup [\text{Neighbors}]^B};$$

$$Y = \frac{[\text{Neighbors}]^B - [\text{Neighbors}]^A}{\text{Max degree in } B};$$

$$\text{and, } Z = \frac{[\text{Neighbors}]^B - [\text{Neighbors}]^A}{[\text{Neighbors}]^B \cup [\text{Neighbors}]^A}$$

such that

NESH=1−(X−(Y+Z))

The component X provides a measure of the extent of neighborhood similarity irrespective of the direction of change, while component Y and Z penalizes X over exclusive enrichment in the set of first neighbors corresponding to the disease (case) set over the healthy (control). The component Y quantifies the exclusive enrichments over the maximum interacting partners a node can have in the disease state (given by the maximum degree in the network). On the other hand, the component Z quantifies the exclusive set enrichments over the union of the interacting partners of the node in the two compared networks. Since, the maximum value for X is 1, the score can be easily translated to a positive scale by subtracting the value of (X−(Y+Z)) from 1. Thus a higher NESH score would account for a higher neighborhood shift for a compared node.

According to an embodiment of the disclosure, the system 100 further comprises the network pair identification module 136. The network pair identification module 136 is configured to identify two things whether the filtered network pair: Firstly, have undergone community shuffling if there is a predefined split in the communities between the two networks using the community shuffling plot and individual community members (nodes) show a change in the value of coreness, and secondly, have undergone rewiring based on the value of the Jaccard edge index. In an embodiment, the Jaccard edge index is less than or equal to 0.5, wherein a lesser the value indicates more the rewiring. The predefined split is defined as the extent to which a microbial community is changed from one state ('control') to other ('case') identified with higher number of low value horizontal cells in the community shuffling plot, wherein when the Y-axis is 'control' and the X-axis is 'case'.

According to an embodiment of the disclosure, the system 100 further comprises the key driver identification module 138. The key driver identification module 138 is configured to identify a node as a key driver from the first network to the second based on a predefined condition depending on the values of the neighbor shift score and the scaled change in betweenness. The predefined condition for determining the key driver is: a higher value of the neighbor shift score indicates a greater change in its interacting partners of a node, and a positive value of the scaled change in betweenness indicates the node to have gained importance in the perturbed state, wherein for the positive value of the scaled change in betweenness, the node having a higher neighbor shift score is considered to be the key driver.

Figure 2A:
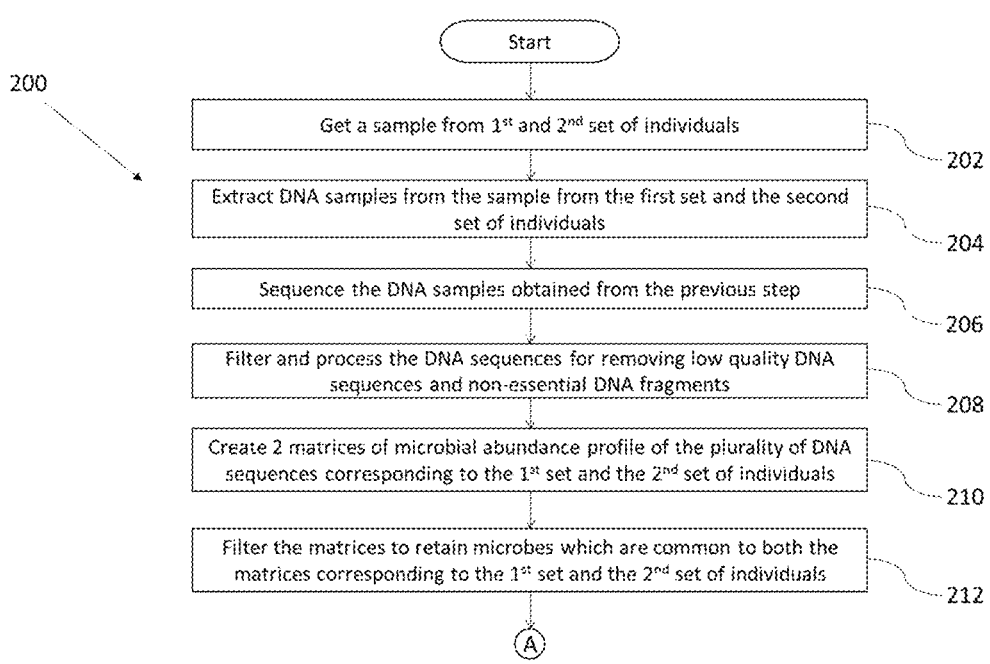
FIGS. 2A, 2B and 2C are a flowchart illustrating the steps involved in identification of key driver responsible for bringing a change in a microbial population according to an embodiment of the present disclosure.
Figure 2B:
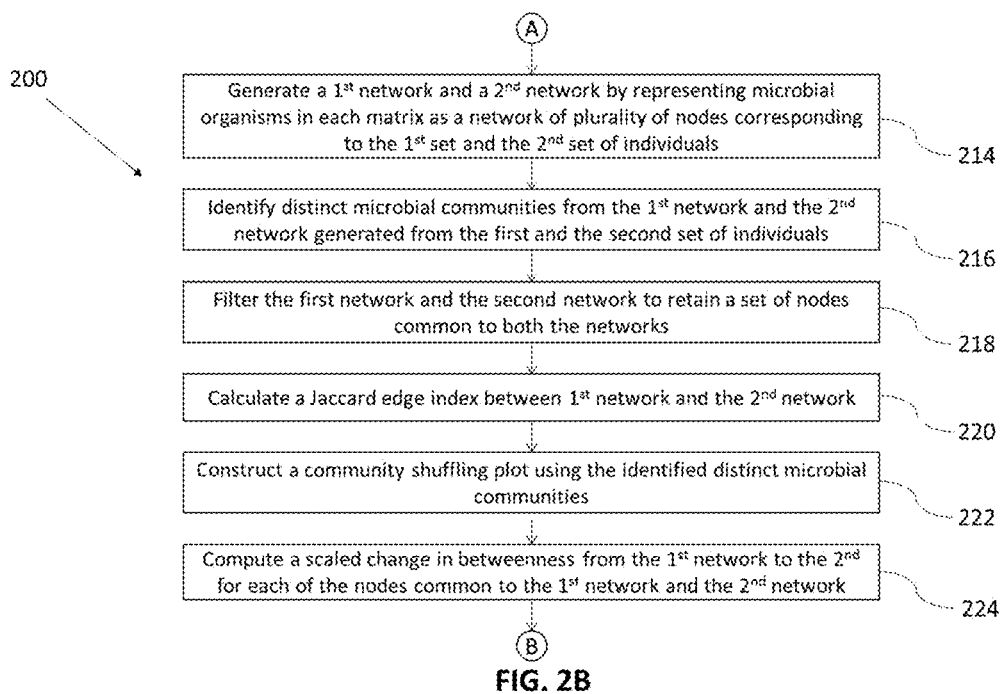
Figure 2C:
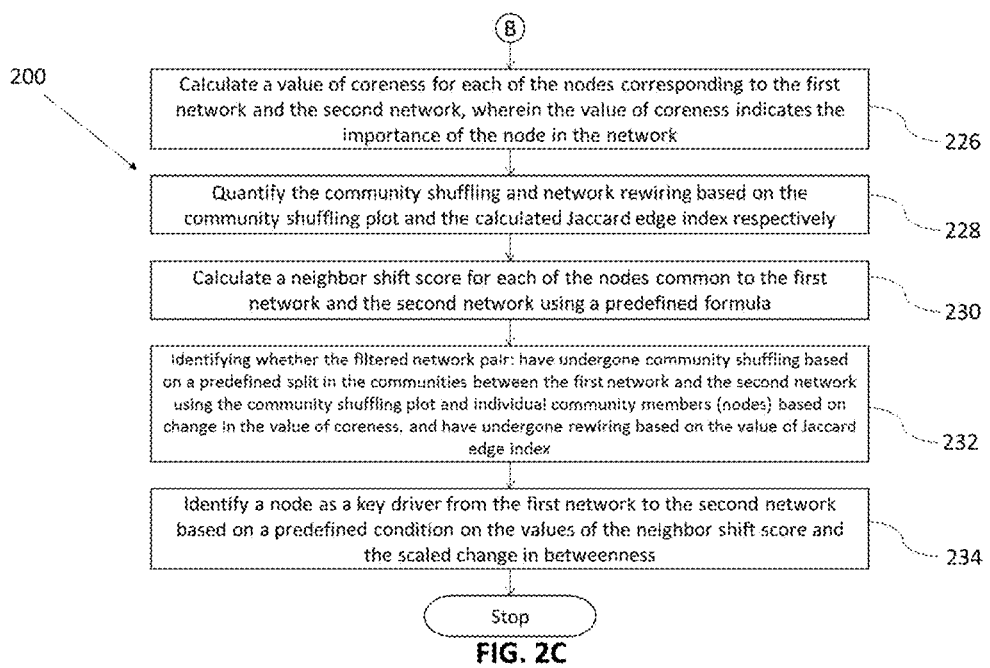

In operation, a flowchart 200 illustrating the steps involved for identification of key driver responsible for bringing a change in a microbial population as shown in FIG. 2A-2C according to an embodiment of the disclosure. Initially at step 202, a sample from a first set of individuals and a second set of individuals is acquired using an input module 102. In an embodiment the first set of individuals are in diseased state while the second set of individuals are in healthy state. Further, the healthy state can be referred as the reference state and the diseased state can be referred as the perturbed state. At step 204, DNA samples are extracted from the samples from the first and the second set of individuals. At the next step 206, each of the DNA samples are sequenced using a throughput sequencer 106 to generate a plurality of DNA sequences. Normally, the DNA sequences obtained in the previous step may contain a lot of reads of low quality, therefore at the next step 208, the plurality of DNA sequences are filtered and processed for removing the low quality DNA sequences and non-essential DNA fragments.

At step 210, two matrices of microbial abundance profile of the plurality of DNA sequences corresponding to the first set and the second set of individuals are created. Each matrix of microbial abundance profile includes abundances of microbial organisms corresponding to individuals belonging to corresponding to the first set and the second set of individuals. The creation of matrices corresponds to identification of counts of all potential microbes across the first set and second set of individuals using a marker gene survey data or a whole genome sequence data. At step 212, the created matrices are filtered to retain microbes which are common to both the matrices corresponding to the first set and second set of individuals.

In the next step 214, the first network and the second network are generated by representing microbial organisms in each matrix as a network of plurality of nodes corresponding to the first set and the second set of individuals. At step 216, distinct microbial communities are identified from the first network and the second network generated from the first and the second set of individuals. The distinct microbial communities are identified using at least one of a fast greedy algorithm, an edge betweenness algorithm or a walk-trap algorithm. In the next step 218, the generated first network and the second network are then filtered to retain a set of nodes common to both the networks.

In the next step 220, the Jaccard edge index is calculated between the first network and the second network. In the next step 222, the community shuffling plot is constructed using the identified distinct microbial communities. The constructed community shuffling plot displays the similarity between the first network and the second network in the form of heat-map and a network view. In the next step 224, a scaled change in betweenness is computed from the first network to the second for each of the nodes common to the first network and the second network. In the next step 226, a value of coreness is calculated for each of the nodes corresponding to the first network and the second network, wherein the value of coreness indicates the importance of the node in the network.

Further at step 228, the community shuffling and network rewiring are quantified. The community shuffling is quantified based on the community shuffling plot, whiles the network rewiring is quantified based on the calculated Jaccard edge index. In the next step 230, the neighbor shift score is calculated for each of the nodes common to the first network and the second network using the predefined formula. In the next step 232, it is identified whether the filtered network pair have undergone community shuffling based on a predefined split in the communities between the first network and the second network using the community shuffling plot and individual community members (nodes) based on change in the value of coreness, and have undergone rewiring based on the value of Jaccard edge index. And finally at step 234, a node is identified as the key driver from the first network to the second network based on a predefined condition on the values of the neighbor shift score and the scaled change in betweenness. The predefined condition is a higher value of the neighbor shift score indicates a greater change in its interacting partners of a node, and a positive value of the scaled change in betweenness indicates the node to have gained importance in the perturbed state, wherein for the positive value of the scaled change in betweenness, the node having a higher neighbor shift score is considered to be the key driver.

The present disclosure provides applicability to various industries. The system and method has immense applicability for meta-genomics researchers as well as researchers working in diverse areas of biological research, ranging from medical microbiology, to industrial and environmental biotechnology. In addition to that, the present disclosure can also be useful for health care professionals, pharmaceutical companies, researchers working in understanding disease pathogenesis, environmental biologists/Organizations involved in bio-remediation, microbial Ecologists, professionals working in industrial microbiology etc.

Figure 3B:
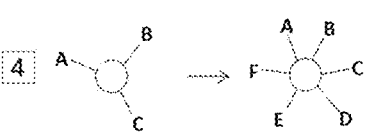

According to an embodiment of the disclosure, the system 100 for identification of the key driver responsible for bringing a change in the microbial population can also be explained with the help of following experimental data:
1. Validation of the NESH Score:

In order to characterize the importance of the NESH score in the context of actual networks, three categories were created, each consisting of three representative conditions. Every condition represents a biologically relevant scenario where a node has a change in interacting partners between a control and case network. As shown in FIGS. 3A, 3B and 3C, the three categories correspond to conditions where a node has similar, higher or lower number of interacting partners between the compared networks respectively. With respect to microbial association networks, these correspond to cases where a microbe shows an altered set of interacting partners in a diseased/perturbed ('case') state. The new partners in the diseased state as a result of the altered interactions hold a greater significance in quantifying the importance of a microbe. When a microbe is associated with a completely different set of partners in the perturbed state, it can be assumed to be a key member or a potential 'driver'. Scenarios 2, 6 and 7 illustrate such cases and have been successfully captured by the NESH score (with high values). Similarly, a lower value is assigned when the altered set of associated nodes in the diseased state (case) shares a higher overlap with those in the control state (as in scenarios 1, 9, 5 and 3). Merely losing a set of associated partners is also assigned a lower score value (scenario 9) as it signifies lowering of importance. Nodes with exactly similar associations are considered neutral to the change and hence are scored lowest (scenario 1). Contrary to the NESH score, the Jaccard index of the neighbors fails to correctly quantify these changes in most cases and is also unable to differentiate several changes (scenario 2-7 and 9-4). In a nutshell, the relative order of NESH score follows s sequence as shown below:

"Same neighbors in both case and control<Sub setting of interacting partners in case with respect to control<All/some same partners+few/some new partners in case with respect to control<completely new (or many new) neighbors"

2. Case Studies with Real World Microbiome Data

Two studies on gut and oral (saliva and plaque) microbiome samples in allergy (asthma) and HIV, respectively, were chosen for the case study. Both dataset had a set of healthy ('control') and diseased ('case') samples and reported no clear cut differences between the case and control states. Hence, the NetShift analysis route was chosen to check whether any additional insights can be obtained from these datasets. Datasets used for the case studies were obtained from the EMBL Microbiome database. The genus level taxonomic abundance files were downloaded and filtered to include genera present in at least 30 percent of the samples. Similar to a differential abundance analysis, genera exclusive to either the case or control datasets were excluded. The final abundance matrices were used to generate the microbial association networks for each datasets using a bootstrap and correlation based approach using CCREPE tool as explained by ES and Weingart G (2014). ccrepe: ccrepe_and_nc.score. R package version 1.15.0. This approach calculates the statistical significance of a correlation (spearman in this case) between a given pair of genera using a re-sampling and null distributions of correlation values (obtained by 1,000 iterations). An edge is assigned between a pair of genera for every predicted significant positive correlation ($p<0.005$).

2a. Analyzing Gut Microbiome for Allergy Dataset

Several recent reports have established the emerging relationship between allergy (asthma, atopy, etc.) and gut microbiome. One of the hypothesized mechanisms relating to this connection pertains to alternation in gut microbial composition which in turn influences allergic immune responses. However, these changes may not always be apparent from the taxonomic composition statistics or abundance based clustering. Analyzing microbial association networks may thus complement in increasing understanding in allergic diseases. A dataset was selected for analysis where 21 adult patients suffering from allergic asthma were studied and compared their fecal microbiota with those from 22 healthy controls. Any clustering or differentially abundant taxa specific to the allergy samples was not found.

Figure 6:
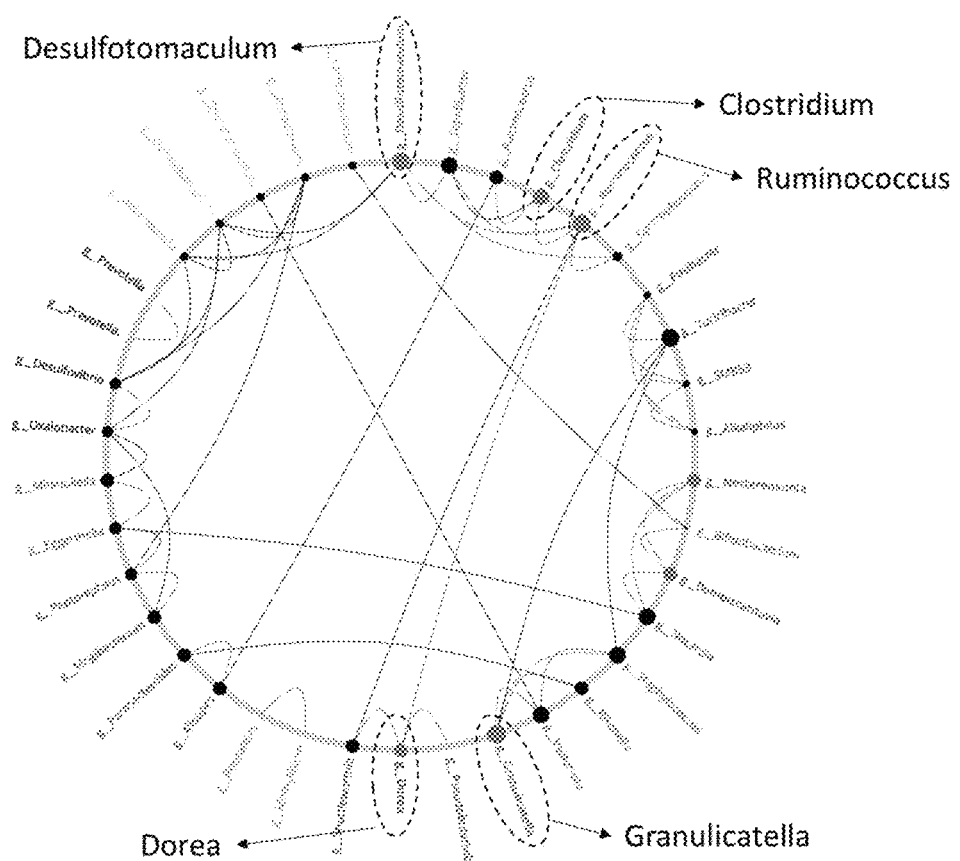
FIG. 6 shows 'driver' genera identified in the allergy dataset showing pathogen colonization as well as colonization resistance by the commensals according to an embodiment of the disclosure.

The microbial association network was generated (as described in the Methods section) for the allergy (case) and healthy (control) sets and applied the NetShift workflow using the implemented web-server. The observed low Jaccard edge index (0.17) pointed towards sufficient rewiring between the two networks. Prominent changes in the community structure were clearly evident from the community shuffling heat-map and network plots as shown in FIG. 4 and FIG. 5 respectively. High density and lower average path length (APL) in the allergy network indicates higher efficiency of information transport in the network which might suggest pathogen colonization. A closer look into the community shuffling network as shown in FIG. 5, it revealed two distinct 'core hub community', one in the control (CONTROL_1) and other in the case network (CASE_2). While the 'CONTROL_1 core hub' consisted of genera namely *Dehalobacterium, Eubacterium, Desulfovibrio* and *Akkermansia*, the 'CASE_2 core hub' was composed of genera *Fusibacter, SMB53, Alkaliphilus* and *Turicibacter*. The member genera in the 'control core hub' are mostly well known gut commensals like *Eubacterium* which is a butyrate producer. *Dehalobacterium* is known to produce acetate from dichloromethane which is utilized mainly by other butyrate-producing bacteria found in the human colon. *Desulfovibrio* is a prominent Sulfate-reducing bacteria (SRB) which helps to maintain redox balance in the gut and *Akkermansia* is the most abundant mucus degrading bacteria found in healthy individuals. On the other hand, genera in the 'case core hub' had well known gut pathogens like *Turicibacter* which are known to be strongly associated with immune function and bowel disease. Additionally, the members of the 'case core hub' were seen to have lower coreness values in the control network as compared to the 'control core hub' as shown in FIG. 5 which might be due to the commensals effort in subduing pathogen colonization. However, in the diseased state (case network), the pathogenic 'case core hub' are seen clearly colonizes and the commensals seizing to be the core members. Interestingly, a closer look into the 'driver genera' between the case and control state, revealed *Ruminococcus, Clostridium, Granulicatella, Desulfotomaculum* and *Dorea* as the top five critical nodes which had a high NESH score and an increase in betweenness. When investigated only for high NESH score nodes (i.e., nodes undergoing high rewiring irrespective of increase in importance), the same taxa were observed except *Dorea* which was replaced by *Turicibacter. Ruminococcus, Clostridium, Desulfotomaculum* and *Dorea* are mostly reported as commensals known to digest resistant starches maintaining gut homeostasis or produce acetates to help other butyrate producing commensals. On the other hand, *Granulicatella*, also observed as one of the 'drivers', is reported to have pathogenic roles. The case specific associations of *Granulicatella* as seen in the union sub-network as shown in FIG. 6 point toward other pathogens like *Staphylococcus* and *Veillonella* also having high NESH scores. The table corresponds to the network shift scores for the identified top five driver nodes (i.e., nodes having positive del betweenness score and higher network shift score) corresponding to "Allergy" is shown in Table I

| Genera name (driver) | Network shift score |
| --- | --- |
| *Granulicatella* | 2.350 |
| *Ruminococcus* | 2.300 |

-continued

| Genera name (driver) | Network shift score |
| --- | --- |
| *Desulfotomaculum* | 2.200 |
| *Clostridium* | 2.067 |
| *Dorea* | 1.733 |

Table I corresponding to Supp, FIG. 3 (Allergy)

The presence of a particular combination and relative abundance of commensal microbes are known to generate distinct immune environments and immune responses in the host and prevent pathogen colonization. However, some pathogens are able to disrupt the resistance and subsequently infect the host especially during disturbed immune response during an infection. The associations of *Turibacter* with the 'case core hub' members and *Granulicatella* might be an indicator of two independent pathogens trying to colonize in the case network but only one becoming a driver. On the other hand, the existence of prominent commensal 'driver' genera might be an effort by them to prevent the pathogen colonization.

2b. Oral Microbiome Analysis in HIV Patients

Recent investigations have strengthened the relationship between the altered microbiome and HIV. In pursuit of understanding the role of oral microbiome in HIV infection, another publicly available study was selected on oral (saliva and plaque) microbiome in HIV individuals. The original study reported the saliva and plaque microbiome to be distinctly different (in both HIV positive and negative individuals). However, neither the oral nor the plaque microbiome was reported to have any difference between the HIV positive and negative groups. For community analysis, in the original study, Jaccard and theta YC distance matrices was used to quantify differences between the case and control groups in the two datasets. However, these matrices may be limited to reproduce only abundance level variations without any weightage to inter microbial associations. Hence, NetShift was used to investigate whether any community level differences are evident to complement the original report.

Figure 7:
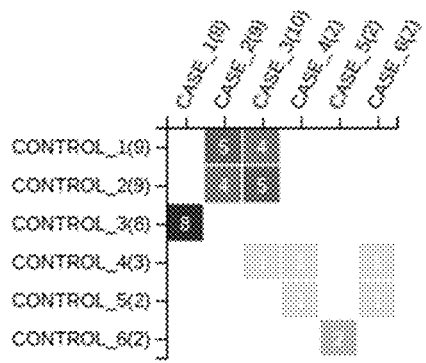
FIG. 7 shows community shuffling heat-map for the saliva and plaque HIV dataset according to an embodiment of the disclosure.
Figure 7:
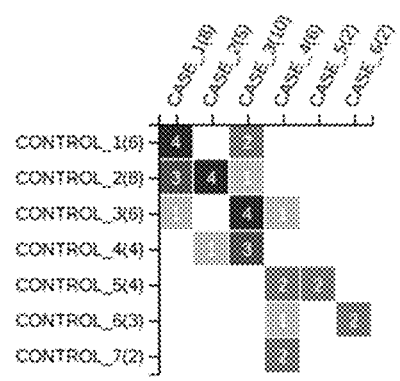
Figure 8:
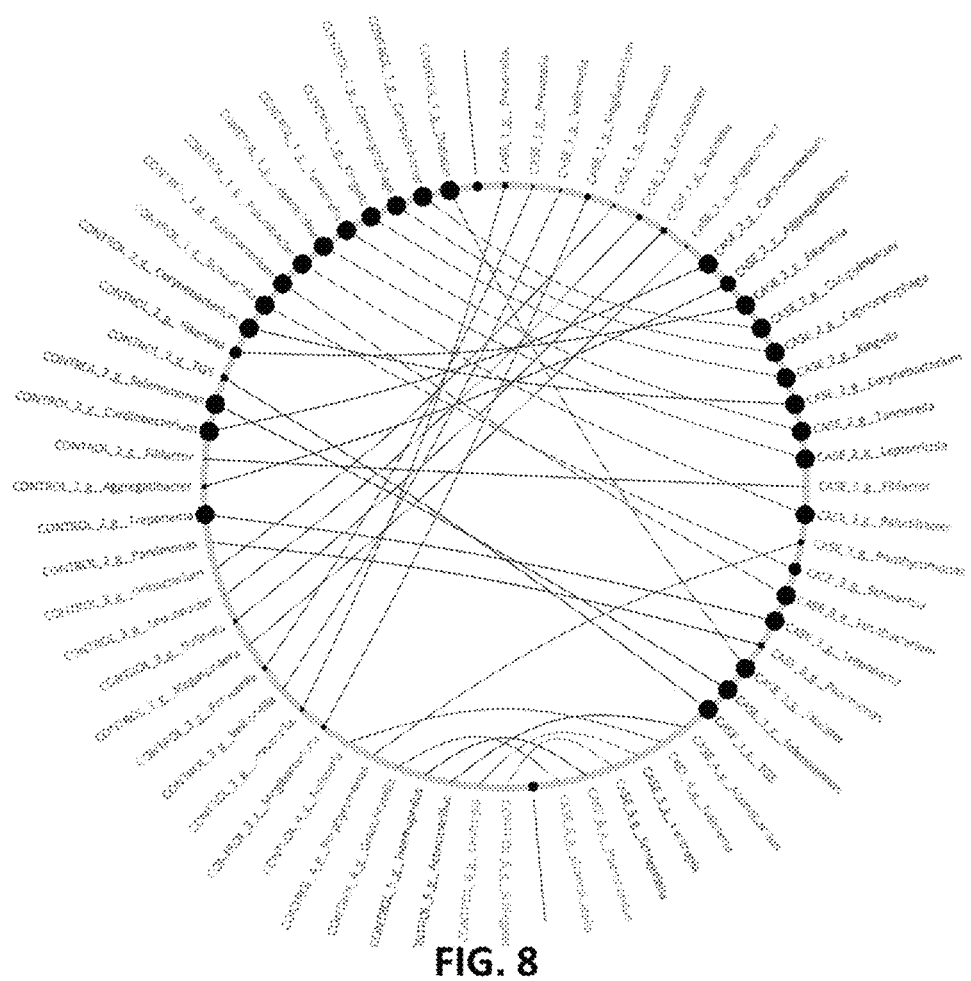
FIG. 8 shows community shuffling graph for the saliva HIV dataset where node sizes are mapped to 'coreness' values according to an embodiment of the disclosure.
Figure 9:
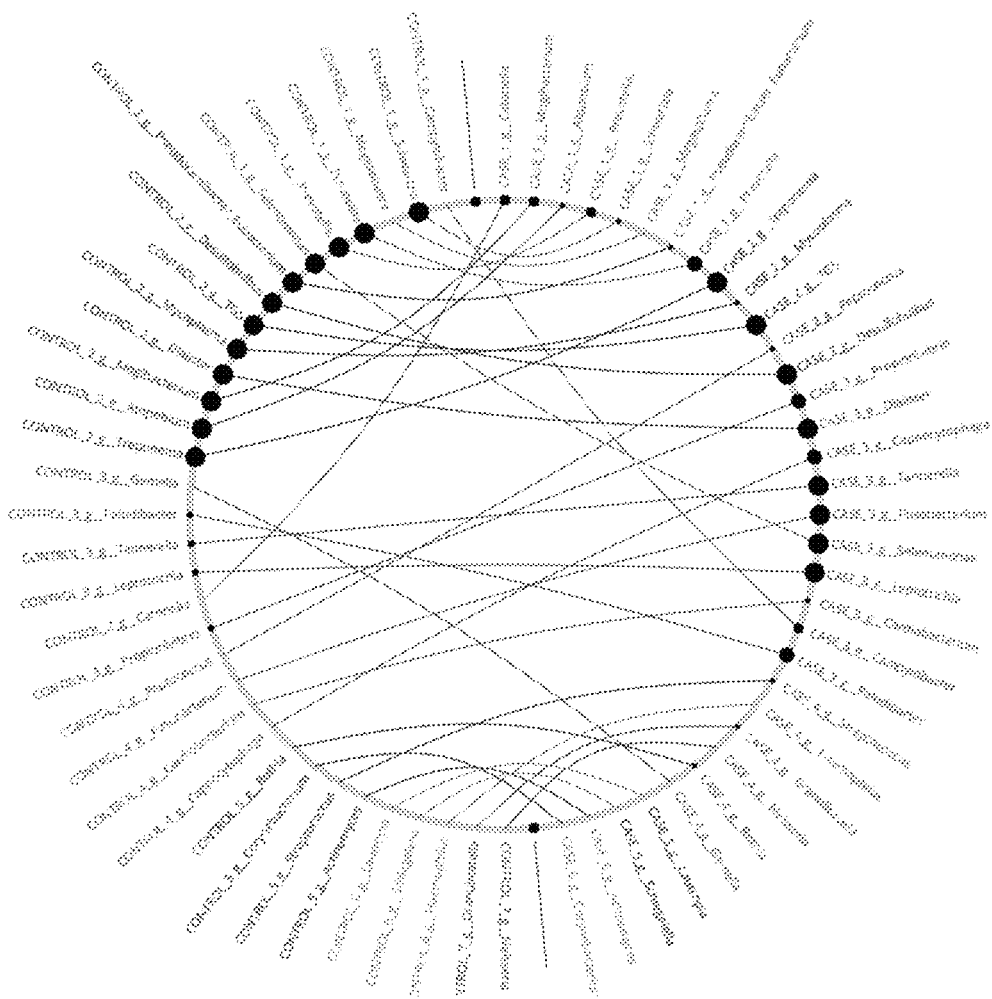
FIG. 9 shows community shuffling graph for the plaque HIV dataset where node sizes are mapped to 'coreness' values according to an embodiment of the disclosure.
Figure 10:
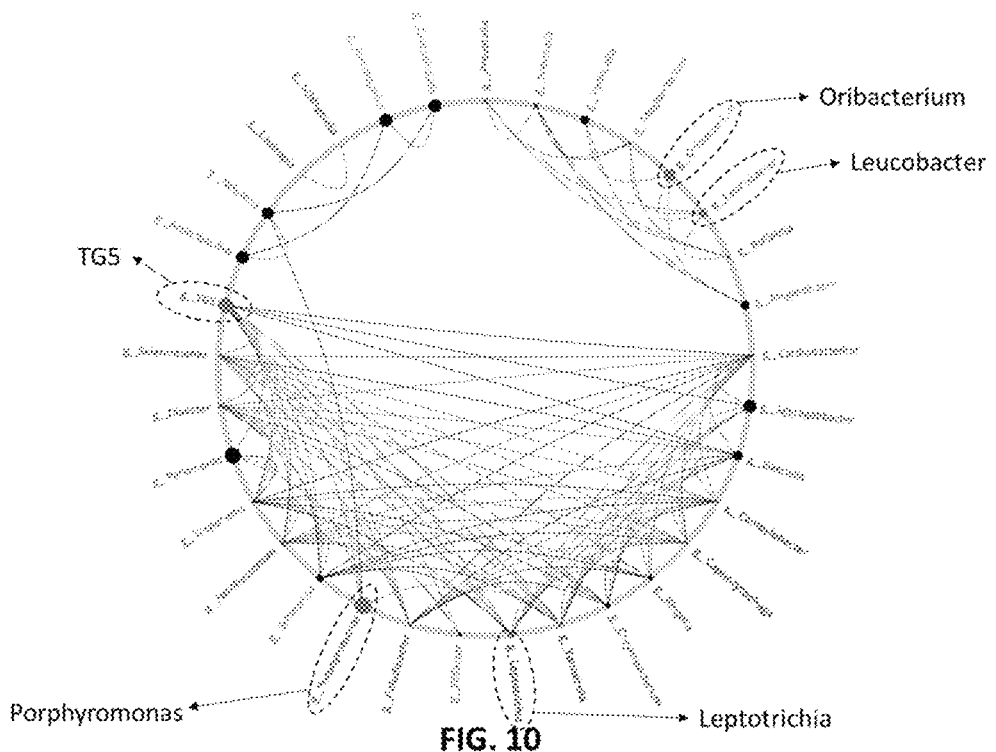
FIG. 10 shows 'driver' genera identified in the saliva HIV dataset showing pathogen colonization according to an embodiment of the disclosure.
Figure 11:
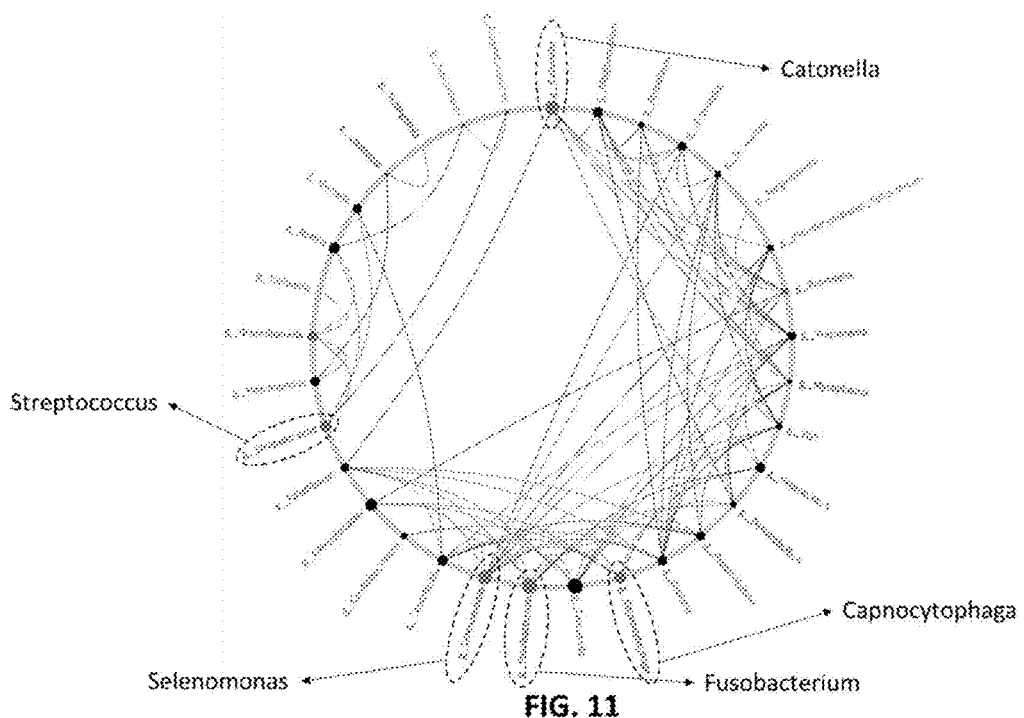
FIG. 11 shows 'driver' genera identified in the plaque HIV dataset showing pathogen colonization according to an embodiment of the disclosure.

The community heat-map plot indeed showed very little community shuffling in the saliva dataset as compared to the plaque as shown in FIG. 7. The network plot also showed more conserved core members in the saliva dataset as shown in FIG. 8 and FIG. 9. However, the Jaccard edge index indicated high rewiring in the plaque (0.228) and a fare amount in the saliva (0.581). Also low APL and high network density in plaque case network provided some signs of pathogen colonisation. While saliva dataset had four distinct drivers *Porphyromonas*, TG5, *Oribacterium* and *Leucobacter*, the plaque dataset showed *Selenomonas, Fusobacterium, Catonella, Capnocytophaga, Streptococcus* and *Granulicatella* as prominent drivers as shown in FIG. 10 and FIG. 11. The table corresponds to the network shift scores for the identified top five driver nodes (i.e., nodes having positive del betweenness score and higher network shift score) corresponding to "HIV-Saliva" and "HIV-Plaque" is shown in Table II and Table III respectively.

| Genera name (driver) | Network shift score |
| --- | --- |
| *Porphyromonas* | 2.067 |
| TG5 | 1.890 |
| *Oribacterium* | 1.467 |

-continued

| Genera name (driver) | Network shift score |
|---|---|
| Leucobacter | 1.133 |
| Leptotrichia | 0.867 |

Table II corresponding to HIV-saliva

| Genera name (driver) | Network shift score |
|---|---|
| Fusobacterium | 2.616 |
| Catonella | 2.403 |
| Selenomonas | 2.357 |
| Capnocytophaga | 2.170 |
| Streptococcus | 2.023 |

Table III corresponding to HIV-plaque

*Porphyromonas*, a major etiologic agent of chronic periodontitis and *Oribacterium* were observed to be a part of two distinct communities in the saliva dataset. Similar relationships were reported in an earlier study on dysimmunity and inflammation in oral lichen planus, a common chronic oral inflammatory disease which is related to HIV infection. On the other hand, the 'drivers' identified in Plaque dataset consisted of genera namely *Selenomonas, Fusobacterium, Catonella* and *Granulicatella*, all of which are well reported periodontal pathogens. Interestingly, periodontal diseases are often reported to be first clinical sign of human HIV infection which is caused by the coordinated action of a complex microbial community resulting in inflammation of tissues supporting the teeth. Thus, the importance of understanding the bacterial component of HIV, their changes in community structure upon HIV invasion and associated differences across diseased and healthy state is expected to provide vital insights in understanding the microbial basis of HIV. The NetShift methodology helps to uncover such hidden community level changes which might be too early to be apparent as a change in abundance profile.

CONCLUSION

The resident microbiome in the human body is known to harbor an ecosystem that fosters host immune development as well as protect it from pathogen colonization, often referred to as colonization resistance. However, the mechanism used by pathogens to overcome these barriers of colonization resistance is still poorly understood. The "keystone pathogen" hypothesis is one such which says that certain low abundant microbial pathogen can orchestrate inflammatory disease by remodeling a normal microbiota into a dysbiotic one. The observations in the allergy microbiome in the case study show some evidences of such pathogen colonization and subsequent disempowerment of the commensals. Similarly, several pathogens identified in the HIV dataset as 'drivers' may serve as early indicators of a pathogen invasion. Studying microbial co-occurrence networks serve as a valuable means for understanding changes in association patterns, which in many cases cannot be inferred based on differential abundances. The present disclosure provides embodiments of a special analysis methodology, called 'NetShift', that can quantify these salient changes and utilize the same to identify taxonomic groups that may act as 'drivers' for a disease.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:
1. A method for identification of a key driver that is responsible for bringing a change in a microbial population, comprising:
receiving a sample comprising a microbiome from a first set of individuals and a second set of individuals, wherein the first set of individuals is in a reference state and the second set of individuals is in a perturbed state;
extracting Deoxyribonucleic acid (DNA) from the received sample of the first set of individuals and the second set of individuals;
sequencing the extracted DNA corresponding to the first set of individuals and the second set of individuals to generate a plurality of DNA sequences;
filtering and processing the generated plurality of DNA sequences corresponding to the received sample of the first set of individuals and the second set of individuals, wherein the plurality of DNA sequences is processed to remove low quality DNA sequences and non-essential DNA fragments of the generated plurality of DNA sequences;

creating two matrices of a microbial abundance profile of the generated plurality of DNA sequences corresponding to the received sample of the first set of individuals and the second set of individuals, wherein
the microbial abundance profile contains abundance values of each of a plurality of microbes present in the sample of the first set of individual and the second set of individuals,
each matrix of the two matrices of the microbial abundance profile includes abundances of the plurality of microbes corresponding to the sample of the individuals belonging to corresponding to the first set of individuals and the second set of individuals,
the microbial abundance profile comprises abundance values of a plurality of individual taxonomic groups in the generated plurality of DNA sequences corresponding to the plurality of microbes of the sample of the first set of individuals and the second set of individuals,
each matrix includes a plurality of rows and a plurality of columns,
the plurality of rows represents the plurality of individual taxonomic groups,
the plurality of columns represents a presence of the plurality of individual taxonomic groups in the corresponding sample, and
the creation of the two matrices corresponds to identification of counts of all potential microbes across the first set individuals and the second set of individuals using a marker gene survey data or a whole genome sequence data;
filtering the created two matrices to retain information of microbes which are common to the created two matrices corresponding to the first set of individuals and the second set of individuals, wherein the filtration of the created two matrices corresponds to exclusion of microbial data which is not present in the first set individuals and the second set of individuals;
generating a first network and a second network by representing the plurality of microbes in each matrix of the created two matrices as a network of plurality of nodes corresponding to the sample of the first set of individuals and the second set of individuals;
identifying distinct microbial communities from the generated first network and the generated second network;
filtering the first network and the second network to retain a set of nodes common to both the generated first network and the generated second network;
calculating a Jaccard edge index between the generated first network and the generated second network, wherein the Jaccard edge index is calculated using:

$$Jaccard\,edge\,index = \frac{A_E \cap B_E}{A_E \cup B_E}$$

where $A_E$ and $B_E$ represent the edge set in the first network and the second network respectively;
constructing a community shuffling plot using the identified distinct microbial communities, wherein the community shuffling plot highlights changes in the identified distinct microbial communities between the first network and the second network association network;
computing a scaled change in betweenness from the first network to the second network for the plurality of nodes common to both the generated first network and the generated second network, wherein computing the scaled change in betweenness is done using a following formula:

$$\Delta B = B_{scaled\,(B)} - B_{scaled(A)}$$

where, $$B_{scaled} = \frac{B_{calculated} - B_{min}}{B_{max} - B_{min}}$$

$B_{calculated}$, $B_{min}$ and $B_{max}$ correspond to the calculated, minimum and maximum betweenness values;
calculating a value of coreness for each of the plurality of nodes corresponding to the first network and the second network, wherein the value of coreness indicates an importance of a node of the plurality of nodes in the network;
quantifying the community shuffling and network rewiring based on the community shuffling plot and the calculated Jaccard edge index respectively;
calculating a neighbor shift score for each of the plurality of nodes common to the first network and the second network using a predefined formula, wherein the predefined formula is:

$$NESH_{(A \to B)} = 1 - \left( \frac{[Neighbors]^A \cap [Neighbors]^B}{[Neighbors]^A \cup [Neighbors]^B} - \left( \frac{[Neighbors]^B - [Neighbors]^A}{Max\,degree\,in\,B} + \frac{[Neighbors]^B - [Neighbors]^A}{[Neighbors]^B \cup [Neighbors]^A} \right) \right)$$

where A and B correspond to the first network and second network generated from each of first and second set of individuals respectively,
$[Neighbors]^A$ and $[Neighbors]^B$ represent the set of first neighbors of the considered node corresponding to A and B respectively;
identifying whether the filtered network pair:
have undergone community shuffling based on a predefined split in the communities between the first network and the second network using the community shuffling plot and individual community members based on change in the value of coreness, and
have undergone rewiring based on the value of Jaccard edge index; and
identifying a specific node of the plurality of nodes as the key driver from the first network to the second network, wherein
the identification is based on a predefined condition on the values of the neighbor shift score and the scaled change in betweenness, and
the key driver brings a change in the microbial population.

2. The method of claim 1, wherein the first set of individuals is in a control state and the second set of individuals is in a case state.

3. The method of claim 1, wherein
the filtration of matrices further corresponds to exclusion of the microbial data present below a minimum specified threshold,
the minimum specified threshold is about 70% of samples in both the sets.

4. The method of claim 1, wherein the distinct microbial communities are identified using at least one of a fast greedy algorithm, an edge betweenness algorithm, or a walk-trap algorithm.

5. The method of claim 1, wherein the constructed community shuffling plot displays a similarity between the first network and the second network in a form of heat-map and a network view.

6. The method of claim 1, wherein the community shuffling is quantified using the community shuffling plot by viewing splits of the communities from the first network to the second network.

7. The method of claim 1, wherein
the value of the Jaccard edge index is less than or equal to 0.5, and
a lesser the value indicates more the rewiring.

8. The method of claim 1, wherein the predefined condition is:
a higher value of the neighbor shift score indicates a greater change in its interacting partners of a node, and
a positive value of the scaled change in betweenness indicates the node to have gained importance in the perturbed state, wherein for the positive value of the scaled change in betweenness, the node having the higher value of the neighbor shift score is considered to be the key driver.

9. The method of claim 1, wherein the predefined split is defined as the extent to which a microbial community is changed from one state ('control') to other ('case') identified with higher number of low value horizontal cells in the community shuffling plot, wherein when the Y-axis is 'control' and the X-axis is 'case'.

10. The method of claim 1, wherein the first network and the second network are generated from each matrices using a bootstrap and correlation based approach using CCREPE tool.

11. The method of claim 1, wherein the distribution of the value of coreness in the first network and the second network are used to identify the communities having a highest change.

12. The method of claim 1, wherein the reference state is a healthy state and the perturbed state is a diseased state.

13. A system for identification of a key driver that is responsible for bringing a change in a microbial population, comprising:
an input module coupled to a processor for receiving a sample comprising a microbiome from a first set of individuals and a second set of individuals, wherein the first set of individuals is in a reference state and the second set of individuals is in a perturbed state;
an extractor extracting Deoxyribonucleic acid (DNA) from the received sample of the first set of individuals and the second set of individuals;
a sequencer for sequencing the extracted DNA corresponding to the first set of individuals and the second set of individuals to generate a plurality of DNA sequences;
a memory; and
the processor coupled with the memory, the extractor, and the sequencer, wherein the processor is further configured to:
filter and process the generated plurality of DNA sequences corresponding to the received sample of the first set of individuals and the second set of individuals, wherein the plurality of DNA sequences is processed to remove low quality DNA sequences and non-essential DNA fragments of the generated plurality of DNA sequences;
create two matrices of a microbial abundance profile of the generated plurality of DNA sequences corresponding to the received sample the first set of individuals and the second set of individuals, wherein
the microbial abundance profile contains abundance values of each of a plurality of microbes present in the sample of the first set of individual and the second set of individuals,
each matrix of the two matrices of the microbial abundance profile includes abundances of the plurality of microbes corresponding to the sample of the individuals belonging to corresponding to the first set of the two matrices and the second set of individuals,
the microbial abundance profile comprises abundance values of a plurality of individual taxonomic groups in the generated plurality of DNA sequences corresponding to the plurality of microbes of the sample of the first set of individuals and the second set of individuals,
each matrix includes a plurality of rows and a plurality of columns,
the plurality of rows represents the plurality of individual taxonomic groups,
the plurality of columns represents a presence of the plurality of individual taxonomic groups in a corresponding microbiome sample, and
the creation of the two matrices corresponds to identification of counts of all potential microbes across the first set individuals and the second set of individuals using a marker gene survey data or a whole genome sequence data;
filter the created two matrices to retain information of microbes which are common the created matrices corresponding to the first set of individuals and the second set of individuals, wherein the filtration of the created two matrices corresponds to exclusion of microbial data which is not present in the first set individuals and the second set of individuals;
generate a first network and a second network by representing the plurality of microbes in each matrix, wherein the filtration of the created two matrices corresponds to exclusion of microbial data which is not present in the first set individuals and the second set of individuals as a network of plurality of nodes corresponding to the sample of the first set of individuals and the second set of individuals;
identify distinct microbial communities from the generated first network and the generated second network;
filter the first network and the second network to retain a set of nodes common to both the generated first network and the generated second network;
calculate a Jaccard edge index between the generated first network and the second network, wherein the Jaccard edge index is calculated using:

$$Jaccard\,edge\,index = \frac{A_E \cap B_E}{A_E \cup B_E}$$

where $A_E$ and $B_E$ represent the edge set in the first network and the second network respectively;

construct a community shuffling plot using the identified distinct microbial communities, wherein the community shuffling plot highlights changes in the identified distinct microbial communities between the first network and the second network association network;

compute a scaled change in betweenness from the first network to the second for each of the nodes common to both the generated first network and the generated second network, wherein computing the scaled change in betweenness is done using a following formula:

$$\Delta B = B_{scaled\ (B)} - B_{scaled(A)}$$

where, $$B_{scaled} = \frac{B_{calculated} - B_{min}}{B_{max} - B_{min}}$$

$B_{calculated}$, $B_{min}$ and $B_{max}$ correspond to the calculated, minimum and maximum betweenness values;

calculate a value of coreness for each of the plurality of nodes corresponding to the first network and the second network, wherein the value of coreness indicates an importance of a node of the plurality of nodes in the network;

quantify the community shuffling and network rewiring based on the community shuffling plot and the calculated Jaccard edge index respectively;

calculate a neighbor shift score for each of the nodes common to the first network and the second network using a predefined formula, wherein the predefined formula is:

$$NESH_{(A \rightarrow B)} = 1 - \left( \frac{[Neighbors]^A \cap [Neighbors]^B}{[Neighbors]^A \cup [Neighbors]^B} - \left( \frac{[Neighbors]^B - [Neighbors]^A}{Max\ degree\ in\ B} + \frac{[Neighbors]^B - [Neighbors]^A}{[Neighbors]^B \cup [Neighbors]^A} \right) \right)$$

where A and B correspond to the first network and second network generated from each of first and second set of individuals respectively, $[Neighbors]^A$ and $[Neighbors]^B$ represent the set of first neighbors of the considered node corresponding to A and B respectively;

a network pair identification module for identifying whether the filtered network pair:
 have undergone community shuffling based on a predefined split in the communities between the first network and the second network using the community shuffling plot and individual community members based on change in the value of coreness, and
 have undergone rewiring based on the value of Jaccard edge index; and
identify a specific node of the plurality of nodes as the key driver from the first network to the second network, wherein
 the identification is based on a predefined condition on the values of the neighbor shift score and the scaled change in betweenness, and
 the key driver brings a change in the microbial population.

14. One or more non-transitory machine readable information storage mediums comprising one or more instructions which when executed by one or more hardware processors cause identification of a key driver that is responsible for bringing a change in a microbial population, the instructions cause:

receiving a sample comprising a microbiome from a first set of individuals and a second set of individuals, wherein the first set of individuals is in a reference state and the second set of individuals is in a perturbed state;

extracting Deoxyribonucleic acid (DNA) from the received sample of the first set of individuals and the second set of individuals;

sequencing the extracted DNA corresponding to the first set of individuals and the second set of individuals to generate a plurality of DNA sequences;

filtering and processing the generated plurality of DNA sequences corresponding to the received sample of the first set of individuals and the second set of individuals, wherein the plurality of DNA sequences is processed to remove low quality DNA sequences and non-essential DNA fragments of the generated plurality of DNA sequences;

creating two matrices of a microbial abundance profile of the generated plurality of DNA sequences corresponding to the received sample of the first set of individuals and the second set of individuals, wherein
 the microbial abundance profile contains abundance values of each of a plurality of microbes present in the sample of the first set of individual and the second set of individuals,
 each matrix of the two matrices of the microbial abundance profile includes abundances of the plurality of microbes corresponding to the microbiome sample of the individuals belonging to corresponding to the first set of individuals and the second set of individuals,
 the microbial abundance profile comprises abundance values of a plurality of individual taxonomic groups in the generated plurality of DNA sequences corresponding to the plurality of microbes of the sample of the first set of individuals and the second set of individuals,
 each matrix includes a plurality of rows and a plurality of columns,
 the plurality of rows represents the plurality of individual taxonomic groups,
 the plurality of columns represents a presence of the plurality of individual taxonomic groups in the corresponding sample, and
 the creation of the two matrices corresponds to identification of counts of all potential microbes across the first set individuals and the second set of individuals using a marker gene survey data or a whole genome sequence data;

filtering the created two matrices to retain information of microbes which are common to the created two matrices corresponding to the first set and the second set of individuals, wherein the filtration of the created two matrices corresponds to exclusion of microbial data which is not present in the first set individuals and the second set of individuals;

generating a first network and a second network by representing the plurality of microbes in each matrix of the created two matrices as a network of plurality of nodes corresponding to the sample of the first set of individuals and the second set of individuals;

identifying distinct microbial communities from the generated first network and the generated second network;

filtering the first network and the second network to retain a set of nodes common to both the generated first network and the generated second network;

calculating a Jaccard edge index between the generated first network and the generated second network, wherein the Jaccard edge index is calculated using:

$$Jaccardedgeindex = \frac{A_E \cap B_E}{A_E \cup B_E}$$

where $A_E$ and $B_E$ represent the edge set in the first network and the second network respectively;

constructing a community shuffling plot using the identified distinct microbial communities, wherein the community shuffling plot highlights changes in the identified distinct microbial communities between the first network and the second network association network;

computing a scaled change in betweenness from the first network to the second network nodes common to both the generated first network and the generated second network, wherein computing the scaled change in betweenness is done using a following formula:

$$\Delta B = B_{scaled\ (B)} - B_{scaled(A)}$$

where, $$B_{scaled} = \frac{B_{calculated} - B_{min}}{B_{max} - B_{min}}$$

$B_{calculated}$, $B_{min}$ and $B_{max}$ correspond to the calculated, minimum and maximum betweenness values;

calculating a value of coreness for each of the nodes corresponding to the first network and the second network, wherein the value of coreness indicates an importance of a node of the plurality of nodes in the network;

quantifying the community shuffling and network rewiring based on the community shuffling plot and the calculated Jaccard edge index respectively;

calculating a neighbor shift score for each of the plurality of nodes common to the first network and the second network using a predefined formula, wherein the predefined formula is:

$$NESH_{(A \to B)} = 1 - \left( \frac{[\text{Neighbors}]^A \cap [\text{Neighbors}]^B}{[\text{Neighbors}]^A \cup [\text{Neighbors}]^B} - \left( \frac{[\text{Neighbors}]^B - [\text{Neighbors}]^A}{\text{Max degree in } B} + \frac{[\text{Neighbors}]^B - [\text{Neighbors}]^A}{[\text{Neighbors}]^B \cup [\text{Neighbors}]^A} \right) \right)$$

where A and B correspond to the first network and second network generated from each of first and second set of individuals respectively, $[\text{Neighbors}]^A$ and $[\text{Neighbors}]^B$ represent the set of first neighbors of the considered node corresponding to A and B respectively;

identifying whether the filtered network pair:
  have undergone community shuffling based on a predefined split in the communities between the first network and the second network using the community shuffling plot and individual community members based on change in the value of coreness, and
  have undergone rewiring based on the value of Jaccard edge index; and identifying a specific node of the plurality of nodes as the key driver from the first network to the second network,
  the identification is based on a predefined condition on the values of the neighbor shift score and the scaled change in betweenness, and
  the key driver is brings a change in the microbial population.

\* \* \* \* \*